United States Patent [19]

Montgomery

[11] Patent Number: 5,262,151
[45] Date of Patent: Nov. 16, 1993

[54] STABILIZED ENZYMATIC ANTIMICROBIAL COMPOSITIONS

[76] Inventor: Robert E. Montgomery, 8916 Hollywood Hills Rd., Los Angeles, Calif. 90046

[21] Appl. No.: 934,772

[22] Filed: Aug. 24, 1992

Related U.S. Application Data

[63] Continuation-in-part of Ser. No. 797,776, Nov. 25, 1991, Pat. No. 5,176,899.

[51] Int. Cl.$^5$ .................. A61K 7/28; A61K 37/50
[52] U.S. Cl. ..................... 424/50; 424/94.4; 426/404; 426/486; 53/403; 53/405; 53/408; 53/932
[58] Field of Search ............. 424/50, 94.4; 426/404, 426/486; 53/403, 405, 408, 92

[56] References Cited

U.S. PATENT DOCUMENTS

| | | | |
|---|---|---|---|
| 2,482,724 | 9/1949 | Baker | 426/10 |
| 2,732,988 | 1/1956 | Feinstein | 226/51 |
| 2,765,233 | 10/1956 | Sarett et al. | 94/178 |
| 3,182,432 | 5/1965 | Canfield | 53/112 |
| 3,430,414 | 3/1969 | Ludwig et al. | 53/79 |
| 3,518,809 | 7/1970 | Ott | 53/112 |
| 4,055,931 | 11/1977 | Myers | 53/22 |
| 4,269,822 | 5/1981 | Pellico et al. | 424/50 |
| 4,537,764 | 8/1985 | Pellico et al. | 424/50 |
| 4,578,265 | 3/1986 | Pellico et al. | 424/50 |
| 4,996,062 | 2/1991 | Lehtonen et al. | 426/8 |
| 5,110,609 | 5/1992 | Lewis et al. | 426/402 |
| 5,176,899 | 1/1993 | Montgomery | 424/50 |

FOREIGN PATENT DOCUMENTS

| | | | |
|---|---|---|---|
| 2520792 | 11/1976 | Fed. Rep. of Germany | 426/10 |
| 986178 | 3/1965 | United Kingdom | 426/404 |

*Primary Examiner*—Shep K. Rose
*Attorney, Agent, or Firm*—Blakely, Sokoloff, Taylor, Zafman

[57] ABSTRACT

A stabilized aqueous composition capable of producing or, in the presence of saliva or other humoral fluid, leading to the production of antimicrobially effective concentrations of hypothiocyanite ions (OSCN—) are herein described. The composition contains an oxidoreductase enzyme and its specific substrate, for the purpose of producing hydrogen peroxide of at least the minimum effective concentration, and in addition, catalase for the destruction of hydrogen peroxide to prevent premature oxidoreductase enzyme decomposition. Optionally, a peroxidase enzyme may be included to act upon the aforementioned hydrogen peroxide, thereby oxidizing thiocyanate ions to produce the antimicrobial concentrations of hypothiocyanite ions (OSCN—).

23 Claims, No Drawings

STABILIZED ENZYMATIC ANTIMICROBIAL COMPOSITIONS

STATEMENT OF RELATED APPLICATION

This application is a continuation-in-part of application Ser. No. 07/797,776 filed on Nov. 25, 1991, now U.S. Pat. No. 5,176,899 issued on Jan. 5, 1993.

BACKGROUND OF THE INVENTION

1. Field of the Invention

This invention relates to antimicrobial compositions which are capable of activating or supplementing naturally occurring peroxidase systems. In particular, compositions which are stable during preparation and after packaging in environments which contain some oxygen, methods of making such compositions, and methods of use are disclosed.

2. Art Background

There is general acceptance as to the etiology of dental caries and periodontal disease in that microflora found in the oral environment are capable of accumulating upon oral surfaces and in unexposed pockets, thriving and producing damaging metabolites in the absence of proper dental hygiene. Colonies of microbes, undisturbed for even short periods of time, are able to aggressively adhere to the surface of enamel, establishing a foothold for further colony growth. Many of the bacterial types commonly found in the mouth secrete polysaccharides such as glucans and dextrans, which form a supportive matrix and thus provide a more mechanically stable environment for further proliferation. Subgingivally, undisturbed colonies of aerobic and anaerobic bacteria can establish similar polysaccharide matrices, in addition to pocket-type formations.

These polysaccharide matrices, together with the thriving microflora contained therein, make up what is commonly referred to as plaque. The first stages in plaque formation occur almost immediately after an enamel surface is scraped, cleaned and polished in dental office tooth cleaning procedures. As colony numbers increase, and the structural integrity of the surrounding polysaccharide matrix evolves, plaque becomes a potential source of bacterial metabolites such as lactic acid. In intimate contact with the enamel surface, acidic plaque metabolites are thus capable of lowering the pH of the enamel surface to a point at which demineralization of the hydroxyapatite can occur. Such demineralization is known to be the cause of tooth decay, also known as caries. Subgingivally, plaque and pocket colonies are known to cause demineralization of both enamel and periodontal bone structure. Gingivitis and periodontitis, infection and irritation of the soft tissues surrounding the teeth, are other clinical manifestations of subgingival plaque and pocket colony proliferation.

One approach taken to decrease caries is by limiting the demineralization of enamel and bone through drinking water fluoridation. It has been shown that the fluoride provided by drinking water (and to a more limited extent, through diet) is capable of being incorporated into hydroxyapatite, the major inorganic component of enamel and bone. Fluoridated hydroxyapatite is less susceptible to demineralization by acids and is thus seen to resist the degradative forces of acidic plaque and pocket metabolites. In addition, fluoride ion concentration in saliva is increased through consumption of fluoridated drinking water. Saliva thus serves as an additional fluoride ion reservoir; in combination with buffering salts naturally found in salivary fluid, fluoride ions are actively exchanged on the enamel surface, further offsetting the effects of demineralizing acid metabolites.

A large body of data indicates that drinking water fluoridation leads to a statistically significant decrease in DMF (decayed, missing, and filled) teeth for a broad range of populations studied. Smaller, less significant effects are seen in fluoridated drinking water studies which examine changes in periodontal health. Positive periodontal effects are thought to arise through the antimicrobial effects of increased fluoride ion concentration in saliva.

However, notwithstanding the established benefits of fluoride treatment of teeth, fluoride ion treatment can result in the mottling of teeth, whether administered systemically through drinking water or topically applied. This effect is known to be both concentration related and patient-specific. In addition, the toxicology of fluoride has recently come under closer scrutiny, although there is no clear answer as to its long term effect on human health. However, for the time being, drinking water fluoridation is believed to serve a wider public good, and its effect on the dental health of populations the world over are pronounced.

Another approach to limiting the proliferation of microflora in the oral environment is through the topical or systemic application of broad-spectrum antibacterial compounds. By killing large numbers of oral microflora, it is postulated, plaque and pocket accumulation, together with their damaging acidic metabolite production, can be reduced or eliminated. The major drawback to such an approach is that there are a wide variety of benign or beneficial strains of bacteria found in the oral environment, which are killed by the same antibacterial compounds in the same manner as the harmful strains. In addition, such treatment with antibacterial compounds may select for certain bacteria and most fungi, which may then be resistant to the antibacterial compound administered, and thus proliferate, unrestrained by the symbiotic forces of a properly balanced microflora population. Such a selected proliferative process leads to yet another clinical problem which must then be addressed with other antimicrobial strategies. Thus, the application or administration of broad-spectrum antibiotics is ill-advised, except in preventative or palliative clinical situations such as oral surgery, severe periodontitis, and immune dysfunction diseases.

Less potent and more selective antimicrobial compounds have been devised, which, when applied topically, have achieved varying degrees of success in checking the growth of harmful oral microorganisms. Of particular interest and relevance to the subject matter of the present invention are those approaches which attempt to activate or supplement the antimicrobial potential of saliva.

Saliva is known to contain a variety of immunoglobulin and non-immunoglobulin antibacterial compounds as a defense against the proliferation of harmful pathogens. Such non-immunoglobulin proteins include lysozyme, lactoferrin and salivary peroxidase. These proteins, or ones similar in function, are found in virtually all mammalian mucosal secretions, providing a first line of defense against pathogenic organisms which would otherwise rapidly proliferate in such warm, moist environments. The enzyme salivary peroxidase, or SPO, functions by utilizing hydrogen peroxide (produced and excreted primarily by certain bacteria as a metabolite, but found also in newly expressed saliva) to oxidize a pseudohalide ion found in saliva, thiocyanate (SCN—), to produce a potent bacteriostatic agent, hypothiocyanite ion (OSCN—). Hypothiocyanite ion and its corresponding acid, hypothiocyanous acid (herein referred to collectively as hypothiocyanite) are able to inhibit the growth of a wide variety of harmful pathogens found in the oral environment. Depending upon the concentration of hypothiocyanite in the saliva, the salivary peroxidase system can either merely inhibit microbial metabolism or actually kill the organism. In general, it has been shown that concentrations of hypothiocyanite greater than about 100 micromoles/liter are sufficient to inhibit the metabolism of plaque bacteria.

Since the salivary peroxidase system, and thus the production of hypothiocyanite, is dependent upon the availability of hydrogen peroxide, various prior art attempts to provide sufficient hydrogen peroxide to activate or supplement the SPO system have been made. Conversely, since SPO begins to show inhibition by concentrations of hydrogen peroxide greater than about 1 millimole/liter, an effective SPO activation mechanism should not provide or accumulate peroxide molarities much higher than this. Direct inclusion of hydrogen peroxide in a mouth rinse composition at these low concentrations has been shown to activate the SPO system for short periods of time (Mansson-Rahemtulla, et al., J. of Dental Res. 62(10): 1062-1066). Another prior art attempt to generate hydrogen peroxide in situ comprised including an oxidoreductase enzyme, such as glucose oxidase, in a dentifrice (Hoogendorn, et al., U.S. Pat. Nos. 4,150,113 and 4,178,519). The glucose oxidase thus provided would, upon oral application, react with glucose present in saliva and in plaque interstitial fluid to produce hydrogen peroxide at low concentrations. Since this approach was dependent upon the availability of glucose in the mouth, a more reproducible and predictable route to enzymatic hydrogen peroxide production was then taken by the present inventor and others by including both glucose oxidase and beta-D-glucose within a dentifrice composition. (U.S. Pat. No. 4,537,764). Beta-D-glucose is the anomer of glucose for which glucose oxidase is specific; in aqueous solution, glucose will mutorotate rapidly to form a mixture of approximately 65% beta-D-glucose and 35% alpha-D-glucose. In order to prevent instability and premature enzyme/substrate interaction the amount of water in the composition had to be limited to less than 10 percent. Upon use of this dentifrice composition, additional water present (from saliva and from water added in the course of normal toothbrushing procedures) would dilute the composition to a water content of greater than 10 percent, thus allowing reaction between glucose oxidase and glucose to ensue. The hydrogen peroxide thus created as a product of reaction would activate the salivary peroxidase system in saliva, producing hypothiocyanite.

Later attempts were made to provide a dentifrice composition containing a complete system of components capable of generating hypothiocyanite in situ (U.S. Pat. Nos. 4,564,519 and 4,578,265). An oxidoreductase enzyme together with its corresponding substrate were combined in a single dentifrice composition with a peroxidase enzyme and a thiocyanate salt, thus providing a method of producing hypothiocyanite independent of fluctuations in salivary glucose, salivary peroxidase and salivary thiocyanate ion. Again, stability of such dentifrice compositions containing a complete enzymatic system capable of producing hypothiocyanite could only be maintained by formulating with less than about 10 percent water. Similarly, the reaction sequence was started by dilution of the dentifrice during toothbrushing.

There are numerous other examples in the prior art of attempts to provide a stable enzymatic dentifrice containing both an oxidoreductase enzyme and its specific substrate for the purpose of producing hydrogen peroxide. Stability of such prior art compositions has been achieved by either limitations placed on the amount of water contained within the composition or by physically separating (through microencapsulation, U.S. Pat. No. 4,978,528) the oxidoreductase enzyme from its specific substrate.

In light of the foregoing description, it would be advantageous to provide a stable, aqueous enzymatic composition capable of supplementing, or, in the presence of saliva or other humoral secretions, activating the peroxidase system in such a fashion that hypothiocyanite ions (OSCN—) are produced in excess of about 100 micromoles/liter/minute in vitro or in vivo.

In addition to the salivary peroxidase system, other natural antimicrobial systems can be found in the humoral secretions of all mammals. These antimicrobial systems consist of a peroxidase enzyme (for example, salivary peroxidase found in saliva and cervical peroxidase found in vertical fluid) together with an oxygen acceptor such as thiocyanate or iodide ion. Both components are normally found in the secretions themselves, and the addition of exogenous hydrogen peroxide activates the system and produces potent antimicrobial species, such as hypothiocyanite and hypoiodite (OSCN— and OI—, respectively).

As described in my prior application referenced above, aqueous compositions capable of producing hydrogen peroxide enzymatically through the action of an oxidoreductase enzyme must be manufactured so as to contain a low level of dissolved oxygen in order to prevent the premature formation of hydrogen peroxide prior to the time of intended use. Such compositions must also be packaged in an essentially anaerobic fashion so as to exclude oxygen during storage. These requirements are the subject of my prior application referred to above.

It would also be advantageous to provide a stable, aqueous enzymatic composition capable of producing or, in the presence of saliva, leading to the production of hypothiocyanite, irrespective of the composition's water content or the amount of water available for dilution upon use. Additionally, formulating latitude and economy would greatly benefit from such aqueous enzymatic dentifrice compositions produced and stabilized without regard to the amount of water contained within the formulation. It would also be advantageous to provide such a composition which may be formulated in the presence of oxygen without having to be particularly careful about removing and/or replacing the oxygen which is present until it is packaged.

It would be of additional utility to provide a method of manufacturing a stable, aqueous enzymatic composition which contains both an oxidoreductase enzyme and its specific substrate, yet prevents hydrogen peroxide accumulation prior to its intended use.

SUMMARY OF THE INVENTION

In accordance with the foregoing description of the prior art and a desire to provide a stabilized aqueous composition capable of producing or, in the presence of saliva, leading to the production of antimicrobial concentrations of hypothiocyanite ions (OSCN—), compositions are herein described which contain both an oxidoreductase enzyme and its specific substrate, for the purpose of producing hydrogen peroxide of at least the minimum effective concentration. The aqueous dentifrice compositions of the present invention can be stabilized against premature enzyme/substrate interaction by controlling the level of dissolved oxygen in the aqueous dentifrice carrier. Optionally, a peroxidase enzyme may be included to act upon the aforementioned hydrogen peroxide, thereby oxidizing thiocyanate ions (found in saliva or optionally included in the present compositions) to produce the antimicrobial concentrations of hypothiocyanite ions (OSCN—).

In the case where the present invention is used as a dentifrice composition, in addition to containing ingredients normally found in dentifrice compositions and well known to those familiar with the art, the aqueous dentifrice compositions of the invention also contain an oxidoreductase enzyme, together with said enzyme's specific substrate, in sufficient quantities to produce hydrogen peroxide at a rate of from about 0.1 millimoles/liter/minute to about 10.0 millimoles/liter/minute during use. The reaction sequence is, in general, as follows:

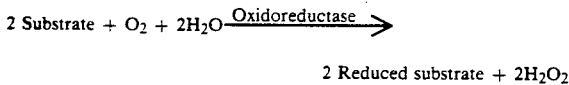

$$2 \text{ Substrate} + O_2 + 2H_2O \xrightarrow{\text{Oxidoreductase}} 2 \text{ Reduced substrate} + 2H_2O_2$$

In addition, the aforementioned compositions may contain a peroxidase enzyme capable of acting upon the enzymatically produced hydrogen peroxide and thereby oxidizing thiocyanate ions (normally found in saliva) to form hypothiocyanite ions (OSCN—). The level of peroxidase enzyme in such compositions shall in the preferred embodiment, be sufficient to, when in contact with saliva (which contains thiocyanate ions), cause the production of at least 100 micromoles/liter/minute of hypothiocyanite ions (OSCN—) during use. Optionally, thiocyanate ions may also be included in the compositions of this invention in an amount sufficient, together with the other inventive ingredients, to produce in excess of about 100 micromoles /liter/minute of hypothiocyanite ions during use. The reaction sequence is, in general, as follows:

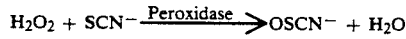

$$H_2O_2 + SCN^- \xrightarrow{\text{Peroxidase}} OSCN^- + H_2O$$

Another aspect of the present invention is that it has been discovered that, irrespective of the amount of water contained in dentifrice compositions comprising an oxidoreductase enzyme together with its specific substrate, premature enzyme/substrate interaction can be eliminated by limiting the amount of dissolved oxygen in the aqueous dentifrice carrier. Thus it is possible to provide an aqueous dentifrice composition containing both an oxidoreductase enzyme and its specific substrate, for the purpose of producing hydrogen peroxide upon use, which will show little or no hydrogen peroxide accumulation in advance of its intended utility. Only upon exposure to additional oxygen will the dentifrice compositions of the present invention be shown to be enzymatically active. The manipulation and control of dissolved oxygen levels in enzymatic dentifrice compositions, for the purpose of limiting an oxidoreductase enzyme/substrate interaction and thereby stabilizing said enzymatic dentifrice until its intended time of use, is unknown in the prior art.

An unexpected benefit of the ability to control the interaction between the oxidoreductase enzyme and its specific substrate by controlling the amount of dissolved oxygen in the aqueous dentifrice carrier, is the possibility of turning the reaction "on" and "off" at any given time in the course of its manufacture. Thus, controlled concentrations of hydrogen peroxide (or alternatively, if additionally formulated with both a peroxidase and thiocyanate ions, hypothiocyanite ions) may be produced in the course of manufacturing in order to reduce any microbial populations without the use of preservatives.

It has been found that the addition or inclusion of catalase (EC 1.11.1.6) in compositions capable of producing hydrogen peroxide enzymatically (such as glucose oxidase and glucose) greatly improves the retention of oxidoreductase activity over the course of manufacturing, packaging and storing the composition. At the point of use, the hydrogen peroxide produced is then consumed almost exclusively by the antimicrobial peroxidases, due to their greater affinity for hydrogen peroxide than catalase.

In general, the ratio of oxidoreductase enzyme to catalase should be in the range of 50 Titrimetric Units of oxidoreductase to 1.0 Baker Unit of catalase, to 2.0 Titrimetric Units of oxidoreductase to 1.0 Baker Unit of catalase (50:1 to 1:1).

One Titrimetric Unit (TU) is defined herein as that amount of oxidoreductase enzyme capable of producing 1.1 micromole of hydrogen peroxide per minute at a temperature of 35° C., and optimal conditions of pH and substrate concentration for each particular oxidoreductase enzyme.

One Baker Unit (BU) is equivalent to that amount of catalase capable of decomposing 264 mg of hydrogen peroxide in one hour under the conditions of the assay (25° C. and pH 7.0)

DETAILED DESCRIPTION OF THE INVENTION

In its simplest form, this invention comprises aqueous compositions containing an oxidoreductase enzyme and a substrate specific to said enzyme for the purpose of producing hydrogen peroxide upon use in combination with catalase for decomposing hydrogen peroxide in the composition. In particular, only those oxidoreductase enzymes which utilize water as a co-reactant and oxygen as an electron donor, thereby producing hydrogen peroxide upon reaction with a specific substrate, are contemplated.

Suitable oxidoreductases include, but are not limited to, glucose oxidase, galactose oxidase, glycollate oxidase, lactate oxidase, L-gulunolactone oxidase, L-2-hydroxyacid oxidase, aldehyde oxidase, xanthine oxidase, D-aspartate oxidase, L-amino acid oxidase, D-amino acid oxidase, monoamine oxidase, pyridoxaminephosphate oxidase, diamine oxidase, and sulfite oxidase. The preferred oxidoreductase is glucose oxidase.

Suitable substrates are specific to the particular oxidoreductase chosen and are well known in the art. For instance, beta-D-glucose is a specific substrate for glucose oxidase. Other suitable substrates include, but are not limited to D-glucose, D-galactose, L-sorbose, ethanol, tyramine, 1, 4-diaminobutane, 6-hydroxy-L-nicotine, 6-hydroxy-D-nicotine, 2-aminophenol, glycollate, L-lactate, 2-deoxy-D-Glucose, L-gulunolactone, L-galactonolactone, D-mannonolactone, L-2-hydroxyisocaproate, acetaldehyde, butyraldehyde, xanthine, D-aspartate, D-glutamate, L-amino acids and D-amino acids.

The inventive dentifrice compositions shall thus contain at least one of the above oxidoreductases and at least one substrate specific to said oxidoreductase, for the purpose of producing hydrogen peroxide at a rate of from about 0.10 millimoles/liter/minute to about 10.00 millimoles/liter/minute during use. Hydrogen peroxide production may be controlled by varying either the concentration of oxidoreductase or the concentration of substrate. For a given rate of hydrogen peroxide production, it is seen to be more economical to increase the level of substrate in the dentifrice composition in order to maximize the rate achievable at a specific oxidoreductase level. Oxidoreductase concentrations may be subsequently increased if substrate enhancement no longer yields a higher or desired rate of hydrogen peroxide production. In general, substrate concentrations may range from about 0.01 percent to about 20 percent or more, by weight of the dentifrice composition.

The compositions of the present invention contain, in general from about 0.10 Titrimetric Units to about 100 Titrimetric Units of an oxidoreductase enzyme per gram of dentifrice.

The hydrogen peroxide producing dentifrice described above may optionally include a peroxidase enzyme for the purpose of utilizing said hydrogen peroxide to oxidize thiocyanate ions (SCN—), which are normally found in saliva, to antimicrobial hypothiocyanite ions (OSCN—). Any peroxidase capable of utilizing hydrogen peroxide to oxidize thiocyanate is contemplated to have utility in the practice of this portion of the invention.

Suitable peroxidases include, but are not limited to, lactoperoxidase, myeloperoxidase, salivary peroxidase, and chloroperoxidase. The preferred peroxidase is lactoperoxidase.

The concentration of peroxidase shall be sufficient to produce hypothiocyanite ions at a rate of about 100 micromoles/liter/minute when interacting with the hydrogen peroxide produced by the oxidoreductase/substrate reaction and the thiocyanate ions found in saliva. In general, the compositions of this invention may contain from 0.10 ABTS Units to about 1000 ABTS Units of peroxidase per gram of dentifrice.

One ABTS Unit, for the purpose herein, is the amount of peroxidase capable of oxidizing one micromole of ABTS (2,2'-azinobis(3-ethylbenzothiazoline-6-sulfonic acid)) per minute at 25° C., 0.1M phosphate buffer (pH 6.0), and initial hydrogen peroxide concentration of 0.100M.

Optionally, the dentifrice compositions described above may contain a thiocyanate ion source in order to provide a complete hypothiocyanite ion producing dentifrice, independent of the availability of such ions in saliva. Thiocyanate ions may be included in the composition at concentrations of from about 0.10 millimoles/gram of dentifrice to about 10.00 millimoles/gram of dentifrice. Thiocyanate ion sources such as sodium thiocyanate, potassium thiocyanate, ammonium thiocyanate, and other thiocyanate salts are contemplated to have utility in such complete systems. The preferred thiocyanate ion sources are potassium thiocyanate and sodium thiocyanate.

In addition to the inventive ingredients described above, the dentifrice compositions of this invention are seen to contain many of the components normally found in such compositions and readily familiar to those skilled in the art. A number of ingredients in the inventive compositions are included or chosen to address the stability requirements for the oxidoreductase and, optionally, the peroxidase enzymes.

Dentifrice compositions of this invention contain a fluid carrier, comprised of water and a humectant, in an amount ranging from about 10% to about 90% by weight of the composition. Suitable humectants include, but are not limited to glycerine, propylene glycol, sorbitol (70% solution), polyethylene glycols, polypropylene glycols, and mixtures thereof. The water content of the composition may typically range from about 5% to about 50% by weight, most preferably from about 10% to about 30% by weight of the total composition.

In order to achieve the desirable aesthetics of flow and flavor release in the final dentifrice composition, a thickener is advantageously included to provide and control viscosity and thixotropy. Suitable thickeners include natural and synthetic water-soluble polymers such as sodium carboxymethylcellulose, xanthan gum, carrageenan, locust bean gum, gum tragacanth, hydroxyethylcellulose (Natrosol, Hercules, Inc.), sodium alginate, starch, polyvinylpyrrolidone, polyacrylic acid (Carbopol, B. F. Goodrich), and others. Inorganic thickeners such as magnesium aluminum silicate (Veegum, R. T. Vanderbilt), hectorites (such as Laponite, La Porte, Ltd.), and hydrated silicas (Sylodent, W. R. Grace), among others, are also useful thickeners for the dentifrice compositions of this invention.

The removal of plaque and tartar by the physical motion of toothbrushing is improved by the inclusion of abrasives in the dentifrice composition. Abrasives commonly included in typical dentifrice compositions are contemplated and include, but are not limited to, calcium pyrophosphate, calcium carbonate, hydrated silica (Sylodent), aluminum hydroxide, dicalcium phosphate dihydrate, tricalcium phosphate, sodium metaphosphate, potassium metaphosphate, aluminum silicate, finely divided poly(methyl methacrylate), and mixtures thereof. In general as is known in the art, the abrasive is present in the composition in concentrations of from about 5% to about 70% by weight, and preferably from about 10% to about 50% by weight of the total composition. A dentifrice's degree of abrasivity can be measured directly or estimated from the RDA (Radioactive Dentin Abrasion) scale. The RDA scale is a measure of an abrasive's ability to erode the surface of enamel after repeated brushing. The higher the RDA score, the more enamel abraded under given conditions. High RDA scores are desired for stain removing dentifrices; low RDA scores are desired for dentifrices for sensitive teeth.

Dentifrices generally contain a foaming agent, or surfactant, to achieve the desired body and texture during toothbrushing. In addition, the surfactant provides a positive psychological impression of the cleansing process, and, to a lesser degree, helps to soften food particles and plaque to assist in their removal by mechanical means. Although desirable, it is by no means necessary to include a surfactant in the dentifrice compositions of this invention. In fact, dentifrice compositions which are not intended to be rinsed following the toothbrushing procedure, such as compositions utilized in veterinary dentistry or oral care products for individuals unable to brush their teeth by normal means, should not contain ingredients, including surfactants, which are not intended or acceptable for ingestion. In those compositions where the presence of a surfactant is desirable, though, compatibility of the surfactant with the enzyme or enzymes of the inventive compositions must be confirmed. Many, but not all, anionic surfactants, such as sodium lauryl sulfate (a commonly employed foaming agent for dentifrice compositions), are known to complex with and inactivate a wide variety of enzymes. Many cationic surfactants are also incompatible with enzymes. In general, nonionic and amphoteric surfactants are preferred in the present dentifrice compositions, as they exhibit, on the whole, much better overall compatibility with enzymes. The prior art addresses the problem of enzyme/surfactant incompatibility at length, and the compatibility of a particular surfactant with the inventive dentifrice compositions must be determined on an individual, compound by compound basis. Surfactants known to be compatible with the enzymatic dentifrice compositions of this invention include, but are not limited to, polysorbate 80, cocoamidopropylbetaine, cocoamphopropionate, sodium lauroyl sarcosinate, ethoxylated (20) isocetyl alcohol, and a wide variety of propylene oxide/ethylene oxide block copolymer nonionic surfactants, such as those offered under the Pluronic tradename by BASF-/Wyandotte Corp.

Since enzymes are more stable and show higher activity at specific pH levels, it is advantageous to provide one or more buffering compounds in the enzymatic dentifrice compositions. Buffers which provide a dentifrice and/or in-use pH of approximately 5.5 to 7.5 are seen to be most beneficial in optimizing the levels of hydrogen peroxide and/or hypothiocyanite ions produced. Any physiologically acceptable buffer providing a dentifrice and/or in-use pH value of from about 5.5 to about 7.5, and preferably between pH 6.0 and pH 7.0, is anticipated having utility in the practice of this invention. The preferred buffers are potassium phosphate, sodium phosphate, disodium phosphate, dipotassium phosphate, and mixtures thereof. The preferred buffer concentrations are from about 0.01 moles to about 1.00 moles/liter of fluid dentifrice carrier (that part of the dentifrice excluding insoluble components such as abrasives).

A wide variety of auxiliary dentifrice components may be included in the present compositions, such as preservatives, whiteners, dyes, fluorides, antitartar and anticalculus agents, chlorophyll compounds, ammoniated materials, and others. Such auxiliary components should be compatible with the components and desired purpose of the enzyme/substrate system of the invention.

A suitable flavoring and/or sweetening material may be employed to achieve the desired aesthetics for the dentifrice. Examples of suitable flavoring components are oils of peppermint, spearmint, clove, wintergreen, cinnamon, sage, eucalyptus and orange. Suitable sweetening agents include saccharin, sodium cyclamate, aspartyl phenylalanine (methyl ester), glucose, xylitol, sucrose, maltose, and others. Flavoring and sweetening agents may comprise from about 0.1% to about 7.0% or more of the dentifrice composition.

As a practical matter, manufacturing should be carried out in a low-oxygen environment, such as a vacuum, or under a nitrogen gas blanket, although such steps are not required.

The dentifrice compositions of this invention are intended to be used or otherwise applied in the manner of normal toothbrushing. Residence or contact time in the oral environment should be at least 30 seconds and preferably from about 60 seconds to 120 seconds or longer. Normally, the dentifrice is rinsed from the mouth following toothbrushing, however, non-rinse or ingestible compositions are anticipated to have utility as previously discussed.

The activities of enzymes are generally measured in terms of micromoles of substrate or co-reactant consumed, or micromoles of product produced, over a given period of time, under specific conditions of temperature, substrate concentration, and co-reactant concentrations. Any description of "unit" activity for a given enzyme should be considered carefully by evaluating a complete description of the conditions under which such activity was measured, and the present invention, as defined by the claims, is considered to be of appropriate scope to encompass the broadest definition of the term.

In light of the aforementioned definitions of Unit activity for oxidoreductases and peroxidases, the compositions of the present invention contain, in general from about 0.10 Titrimetric Units to about 100 Titrimetric Units of an oxidoreductase enzyme per gram of dentifrice, and, optionally, from about 0.10 ABTS Units to about 1,000 ABTS Units of a peroxidase enzyme per gram of dentifrice.

An example of such a composition is a toothpaste which contains glucose and glucose oxidase for the purpose of producing hydrogen peroxide upon use. The inclusion of catalase in example 2 below demonstrates improved stability compared to Example 1. Both Examples 1 and 2 were manufactured under a partial vacuum (20" Hg) and packaged in foil/plastic laminated toothpaste tubes.

EXAMPLE 1

| INGREDIENT | PERCENTAGE/AMOUNT |
| --- | --- |
| Sorbitol 70% | 37.44% |
| Glycerin 96% | 16.00 |
| Dionized water | 16.77 |
| Sodium carboxymethylcellulose 9M31XF | 1.00 |
| Sylodent 750 | 12.00 |
| Sylodent 2 | 12.00 |
| Dextrose | 2.00 |
| Titanium dioxide | 0.40 |
| Other ingredient | 2.39 |
| Glucose oxidase | 6.0 TU/gm paste |
| Catalase | 0.06 BU/gm paste |

EXAMPLE 2

| INGREDIENT | PERCENTAGE/AMOUNT |
| --- | --- |
| Sorbitol 70% | 37.44% |
| Glycerin 96% | 16.00 |
| Dionized water | 16.77 |
| Sodium carboxymethylcellulose 9M31XF | 1.00 |
| Sylodent 750 | 12.00 |
| Sylodent 2 | 12.00 |
| Dextrose | 2.00 |
| Titanium dioxide | 0.40 |
| Other ingredients | 2.39 |

| INGREDIENT | PERCENTAGE/AMOUNT |
|---|---|
| Glucose oxidase | 6.0 TU/gm paste |
| Catalase | 1.0 BU/gm paste |

Example 2 retained over 95% of its original glucose oxidase activity when stored at 35° C. for 14 days, while Example 1 retained less than 8% of its original activity under the same conditions.

The foregoing description of the invention is intended to be exemplary with respect to certain preferred embodiments and it will be understood that modifications and variations thereof obvious to those skilled in the art are to be included within the scope of this application and the appended claims.

What is claimed is:

1. An antimicrobial dentifrice composition made by the process comprising the steps of:
    providing a fluid carrier comprising an oxidoreductase enzyme, an oxidoreductase enzyme substrate and a catalase, wherein said enzyme and substrate form hydrogen peroxide when reacted together in the presence of oxygen, said hydrogen peroxide being formed at a rate of at least 100 micromoles per liter per minute, said oxidoreductase enzyme being present in said composition in the amount of at least 1.0 Tritrmetric Unit per gram of dentifrice, and wherein said catalase is provided in a ratio of about 50 Titrimetric Units oxidoreductase enzyme to 1.0 Baker Unit of catalase, to 1.0 Titrimetric Units oxidoreductase enzyme to 1.0 Baker Unit of catalase to substantially minimize the amount of hydrogen peroxide produced in said composition during storage; and
    storing said mixture in an oxygen impervious container.

2. The composition of claim 1 wherein catalase is provided in an amount in the ratio range of 50 Titrimetric Units of oxidoreductase to 1.0 Baker Unit of catalase, to 1.0 Titrimetric Units of oxidoreductase to 1.0 Baker Unit of catalase.

3. The composition of claim 2 wherein the ratio of oxidoreductase to catalase is about 6.0 Titrimetric Units of oxidoreductase to 1.0 Baker Unit of catalase.

4. The composition of claim 1 further comprising a peroxidase enzyme for oxidizing thiocyanate ions to hypothiocyanite ions.

5. The composition of claim 1 wherein said oxidoreductase is selected from the group consisting of glucose oxidase, galactose oxidase, glycollate oxidase, lactate oxidase, L-gulunolactone oxidase, L-2-hydroxyacid oxidase, aldehyde oxidase, xanthine oxidase, D-aspartate oxidase, L-amino acid oxidase, D-amino acid oxidase, monoamine oxidase, pyridoxaminephosphate oxidase, diamine oxidase, and sulfite oxidase.

6. The composition of claim 1 wherein said oxidoreductase is glucose oxidase.

7. The composition of claim 1 wherein said substrates are specific to the particular oxidoreductase and are selected from D-glucose, D-galactose, L-sorbose, ethanol, tyramine, 1, 4-diaminobutane, 6-hydroxy-L-nicotine, 6-hydroxy-D-nicotine, 2-aminophenol, glycollate, L-lactate, 2'-deoxy-D-Glucose, L-gulunolactone, L-galactonolactone, D-mannonolactone, L-2-hydroxyisocaproate, acetaldehyde, butyraldehyde, xanthine, D-aspartate, D-glutamate, L-amino acids and D-amino acids.

8. The composition of claim 1 wherein said oxidoreductase is glucose oxidase and said substrate is D-glucose.

9. The composition of claim 3 wherein the peroxidase enzyme is selected from lactoperoxidase, myeloperoxidase, salivary peroxidase, and chloroperoxidase.

10. The composition of claim 9 wherein the peroxidase is lactoperoxidase.

11. The composition of claim 1 wherein the catalase is derived from A. niger fermentation.

12. The composition of claim 1, wherein said composition comprises a fluid carrier, comprised of water, in an amount ranging from about 10% to about 90% by weight of the composition.

13. The composition of claim 1 further comprising a humectant selected from glycerine, propylene glycol, sorbitol (70% solution), polyethylene glycols, polypropylene glycols, and mixtures thereof.

14. The composition of claim 12 wherein said water comprises in the range from about 5% to about 50% by weight of said composition.

15. The composition of claim 1 further comprising a thickener selected from natural and synthetic water-soluble polymers selected from sodium carboxymethylcellulose, xanthan gum, carrageenan, locust bean gum, gum tragacanth, hydroxyethylcellulose, sodium alginate, starch, polyvinylpyrrolidone and polyacrylic acid and inorganic thickeners selected from magnesium aluminum silicate, hectorites and hydrated silicas.

16. The composition of claim 1 further comprising abrasives selected from the group consisting of calcium pyrophosphate, calcium carbonate, hydrated silica, aluminum hydroxide, dicalcium phosphate dihydrate, tricalcium phosphate, sodium metaphosphate, potassium metaphosphate, aluminum silicate, finely divided poly(methyl methacrylate), and mixtures thereof.

17. The composition of claim 1 wherein said composition further comprises a physiologically acceptable buffer.

18. The composition of claim 17 wherein said physiologically acceptable buffer is selected from potassium phosphate, sodium phosphate, disodium phosphate, dipotassium phosphate, and mixtures thereof.

19. The composition of claim 1 further comprising additives selected from the group comprising preservatives, whiteners, dyes, fluorides, antitartar and anticalculus agents, chlorophyll compounds, ammoniated materials, flavorings and sweeteners.

20. Method of making a dentifrice composition comprising the steps of:
    mixing together an oxidoreductase enzyme, an oxidoreductase enzyme substrate and a catalase, wherein said enzyme and substrate form hydrogen peroxide when reacted together, said hydrogen peroxide being formed at a rate of at least 100 micromoles per liter per minute said oxidoreductase enzyme being present in said composition in the amount of at least 1.0 Titrimetric Unit per gram of dentifrice and wherein said oxidoreductase enzyme and catalase are present in a fluid carrier in a ratio of about 50 Titrimetric Units oxidoreductase enzyme to 1.0 Baker Unit of catalase, to 1.0 Titrimetric Units oxidoreductase enzyme to 1.0 Baker Unit of catalase; and
    storing said mixture in an oxygen impervious container.

21. The method of claim 20 wherein the composition is made either under a partial vacuum or in an oxygen free atmosphere after said oxidoreductase enzyme and an oxidoreductase enzyme substrate are added thereto.

22. The method claim 21 wherein said step of limiting the amount of oxygen in said composition is performed under an inert gas.

23. An anaerobically packaged composition with an antimicrobial system comprising:

a fluid carrier comprising an oxidoreductase enzyme and an oxidoreductase enzyme substrate, wherein said enzyme and substrate form hydrogen peroxide when reacted together in the presence of oxygen, said hydrogen peroxide is formed at a rate of at least 100 micromoles per liter per minute; and catalase provided in sufficient amount to substantially reduce the amount of hydrogen peroxide in said composition;

said composition being packaged in an oxygen impervious package or container.

* * * * *